United States Patent [19]

D'Andrea et al.

[11] Patent Number: 5,395,366

[45] Date of Patent: Mar. 7, 1995

[54] SAMPLING CAPSULE AND PROCESS

[75] Inventors: David T. D'Andrea, Amherst; Jerome J. Schentag, Eggertsville, both of N.Y.

[73] Assignees: The State University of New York, Albany; Gastrotarget Corp., Tonawanda, both of N.Y.

[21] Appl. No.: 179,502

[22] Filed: Jan. 10, 1994

Related U.S. Application Data

[63] Continuation-in-part of Ser. No. 707,842, May 30, 1991, Pat. No. 5,279,607.

[51] Int. Cl.$^6$ ............................................. A61K 9/22
[52] U.S. Cl. .................................. 604/890.1; 604/93; 604/114; 604/891.1
[58] Field of Search ................ 128/630, 631, 654, 655, 128/737, 903; 604/67, 93, 113, 145, 890.1, 890.1, 892.1; 600/2, 3, 7

[56] References Cited

U.S. PATENT DOCUMENTS

| | | | |
|---|---|---|---|
| 3,212,496 | 10/1965 | Praston | 128/631 |
| 3,659,600 | 5/1972 | Merrill | 604/93 |
| 3,893,111 | 7/1975 | Cotter | 128/631 |
| 3,923,060 | 12/1975 | Ellinwood, Jr. | 128/DIG. 13 |
| 4,146,029 | 3/1979 | Ellinwood, Jr. | 604/891.1 |
| 4,262,632 | 4/1981 | Harton et al. | 128/631 |
| 4,373,527 | 2/1983 | Fischell | 604/891.1 |
| 4,425,117 | 1/1984 | Hugemann et al. | 604/93 |
| 4,439,197 | 3/1984 | Honda et al. | 128/655 |
| 4,447,224 | 5/1984 | DeCant, Jr. et al. | 604/67 |
| 4,507,115 | 3/1985 | Kambara et al. | 604/93 |
| 4,564,363 | 1/1986 | Begnall et al. | 604/93 |
| 4,844,076 | 7/1989 | Lesho et al. | 128/631 |
| 5,279,607 | 1/1994 | Schentag et al. | 604/890.1 |

FOREIGN PATENT DOCUMENTS 3809482 10/1989 Germany ............................ 604/145

OTHER PUBLICATIONS

European Journal of Clinical Pharmacology, vol. 30, pp. 691–697.

Gut, 1960, 1, 266, Wireless Telemetering from the Digestive Tract.
J. Biomed. Eng., 1982, vol. 4, Jul., pp. 247–251.
The American Journal of Medicine, Nov. 30, 1989, vol. 87 (Sup. 5A), pp. 66S–69S.
Biotelemetry Patient Montig 8:213–227 (1981).
The Heidelberg Capsule Used for the Diagnosis of Peptic Diseases, by H. G. Noller, M.D.
Aerospace Medicine, Feb. 1964, pp. 115–117.
Science, vol. 156, 21 Apr. 1967, pp. 351–360, Implant Biotelemetry and Microelectronics.
Physiology and Behavior, 1970, vol. 5, pp. 709–712.
Med. Klin. 59(1964) Nr. 16, pp. 663–666.
Electroenceph. Clin. Neurophysiol., 1967, 22:275–277.
Aerospace Medicine, May 1968, pp. 488–492.
IEEE Transactions on Bio-Medical Engineering, vol. BME-14, No. 4, Oct. 1967, pp. 230–238.
Electroenceph. Clin. Neurophysiol., 1974, 37, pp. 153–160.
Dtsch. Med. Wschr., 85, Jg., Nr39, 23 Sep. 1960, pp. 1707–1713.
Biotelemetry 1:50–59 (1974).
Biotelemetry 1:60–64 (1974).

(List continued on next page.)

Primary Examiner—C. Fred Rosenbaum
Assistant Examiner—Manuel Mendez
Attorney, Agent, or Firm—Crossetta & Associates

[57] ABSTRACT

An ingestible capsule and process for sampling, particularly repeatable sampling, of fluids in the alimentary canal is disclosed wherein an essentially non-digestible capsule contains an electric energy emitting means, a radio signal transmitting means, a sampling storage means and a remote actuatable sampling means. The capsule signals a remote receiver as it progresses through the alimentary tract in a previously mapped route and upon reaching a specified site is remotely triggered to capture a fluid sample in the alimentary canal.

55 Claims, 8 Drawing Sheets

OTHER PUBLICATIONS

Biotelemetry 1:41–49 (1974).
Biotelemetry 1:31–40 (1974).
Proceedings of the Physiological Society, Apr. 1969, pp. 5P–6P.
Psychophysiology, vol. 11, No. 3, May 1974, pp. 382–387.
Minerva Medica—390, pp. 3705–3708.
Elektro Medizin 7:230–235, 1962.
Medical Research Engineering, Mar./Apr. 1969, pp. 9–15.

"A Completely Implantable Three Channel Temperature Biotelemetry System" by J. R. Decker & M. F. Gillis.

"Experiences with the Konigsberg Temperature Pill in Exercising Subjects" by K. Dormer & R. Ratcliff.

"Use of the Heidelberg Capsule for Noninvasive Monitoring of Intragastric pH and Gastric Emptying", Sep. 10–13, 1987.

"Ingestible Telemetry Systems Workshop", Jan. 7, 1988.

SAMPLING CAPSULE AND PROCESS

This application is a continuation-in-part of U.S. patent application Ser. No. 07/707,842, filed May 30, 1991, and now U.S. Pat. No. 5,279,607.

FIELD OF THE INVENTION

This application relates to a novel capsule and process for its use in the precise placement and telemetric gathering of samples in the alimentary canal of animals, particularly humans.

BACKGROUND OF THE INVENTION

There has been a continuing need for a non-invasive means for taking samples of fluids, slurries and the like at precise selected sites in the animal alimentary canal. Generally, such sampling has been achieved by the use of tubes, syringes, endoscopic instrumentation and the like which are generally seen as stressful to the animal and undesirably invasive. Further, such means typically require tracking by undesirable radiation emission means and are highly dependent upon the manipulative skills of the physician gathering the sample and thus prone to human error.

The mechanical devices, which are preferred when the sampling is desired to occur at a specific site, are awkward implements, typically comprising long invasive needles or flexible tube mechanisms which are inserted into the alimentary canal with mechanically operated sampling means at the inserted end. The flexible devices are typically "snaked" into the alimentary tract through the mouth, nose or anal opening and generally require anesthetizing procedures to be acceptable to the animal being treated. Sampling, at a specific site in the tract, requires significant skill and typically must be done using elaborate locating means such as miniaturized video, fluoroscopic, X-ray apparatus or the like.

The medical profession has long recognized the need for more reliable means for the sampling of fluids, slurries and the like at specific alimentary canal sites, particularly means that might be accurately and repeatedly accomplished without confining the patient to a medical facility and without requiring the intensity of medical professional attention now required by typically available mechanical means.

In recent years, "radio pill" technology has been described wherein a capsule, containing a transmitter, has been seen by the medical profession as a possible means to monitor various body environments. It has been suggested that such pills could be implanted, ingested or otherwise placed at desirable locations in the body and could be engineered to transmit critical data to a remote receiver located outside the body. The ideal radio pill is seen as one that is small enough to be easily ingested, biologically inert, disposable and inexpensive. The transmission signal would have to be sufficiently strong to be received by a remote receiver, preferably located apart from the patient's body so that the patient would have freedom of movement, or, by a receiver small enough to be carried by the patient.

As a result of such recent perceptions, researchers from Heidelberg University developed a capsule and system for monitoring pH of the gastrointestinal tract. This capsule and system, generally known as the Heidelberg pH capsule system, comprises a capsule containing a transmitter that is sensitive to pH changes experienced within the gastrointestinal tract. The patient wears a belt, which contains an antenna for collection of transmitted signals, which in turn feeds the signals to a receiver. The receiver stores and/or records the data, generally on a graph, thus providing the medical professional with a non-invasive means to monitor pH within the alimentary canal. Geographic location is not determined using the radio signals. Though the Heidelberg capsule system does allow some freedom of movement for the patient, it requires tethering of the patient to bulky machinery and has not enjoyed widespread commercial success, probably because of the limited use for the information gathered.

Another radio pill that has been recently developed is that generally known as the Konigsberg temperature telemetry pill. The Konigsberg pill is an ingestible capsule comprising a transmitter that is sensitive to temperature changes. As with the Heidelberg capsule, signals are transmitted to a collecting antenna and then to a receiver where the data is stored and/or recorded for use by the medical professional. Again, as with the Heidelberg capsule, geographic location of the capsule is not determined using the radio signals.

Each of the Heidelberg and Konigsberg capsules have utility in the short term monitoring of pH, but neither have the ability to collect a sample at a selected site.

An object of the present invention is to provide a capsule which is easily ingestible in an animal alimentary canal and can be remote triggered to collect a sample of fluid, slurry or the like at a specified site in the canal.

Another object of the invention is to provide a capsule that can transmit a signal to a remote receiver, sufficient to determine geographic location of the capsule within the alimentary canal.

A further object of the invention is to provide a process for the tracking of a capsule through the alimentary canal.

A still further object of the invention is to provide a process for tracking a capsule through the alimentary canal and gather a desired fluid sample at a specified site within the canal.

These and other objects of the invention will become apparent from the following description of the invention.

SUMMARY OF THE INVENTION

The present invention features an ingestible capsule having an exterior surface configured for convenient passage through the alimentary canal, said capsule comprising, an electric power source, a radio signal transmitting means, a remote actuatable activating means, fluid sample storage means and a sampling means, encased in an essentially non-digestible outer shell.

In the system of the invention, the electric power source in the capsule, provides operating power to the transmitting means, which emits radio signals from the capsule that are collected by antennae, exterior to the human body, and fed to an appropriate remote receiver. The capsule containing such transmitter is ingested in the alimentary canal and remote antennae, typically arranged about the body of the animal, collect signals from the capsule at various intensity and direction to provide tracking information to the remote receiver. The remote receiver in turn amplifies, distinguishes and/or converts all or portions of the signals to usable data which is provided to storage and/or comparator means, typically comprising a central process unit such as a computer. The comparator, compares the data from the receiver with previously obtained data pertaining to geographic positions within the alimentary canal contained in the storage means and computes or confirms location. Upon receipt of signals from the capsule indicating alignment of the capsule at a specified site in the alimentary canal, remote means actuates the remote actuatable activating means of the capsule, which in turn actuates the sampling means causing the sampling means to withdraw fluid from the alimentary canal into the capsule.

As can be seen from the aforesaid recitation, the process of the invention generally comprises obtaining directional data, from the passage of a signal transmitting capsule through an alimentary canal, to create a precise map of the routing of the capsule to a precise location in the canal. This directional data is stored and compared to directional data from a subsequent signal transmitting capsule or capsules carrying sampling means passing through the alimentary canal at a later time. Thus, once the route has been mapped and stored, the passage of subsequent capsules can be accurately repeated and the precise sampling of fluids at a selected site can be accurately achieved through multiple repetitions.

The advantage of such process is particularly applicable with a patient that requires periodic sampling of fluids at a specific location in the gastrointestinal tract. Such patient typically receives a first exploratory treatment in a controlled office environment wherein a signal transmitting capsule is ingested and passed through the alimentary canal with its geographic route being mapped to the precise route that the capsule would take to a specific location in the canal. The mapped route is then stored in the computer for further reference. Thereafter, treatment comprises ingestion of a sampling means containing capsule, in a loosely controlled environment, and computer controlled activation of sampling from a remote triggering device at the appropriate arrival of the capsule at the desired site. Significantly, using differential signals, two or more capsules can be contained in the alimentary canal at the same time, providing means to sample and/or to provide medicament dosing at the same or different sites at the same or varying times.

BRIEF DESCRIPTION OF THE DRAWINGS

The nature and mode of operation of the present invention will now be more fully described in the following detailed description taken with the accompanying drawings wherein.

DESCRIPTION OF THE PREFERRED EMBODIMENT

Figure 1:
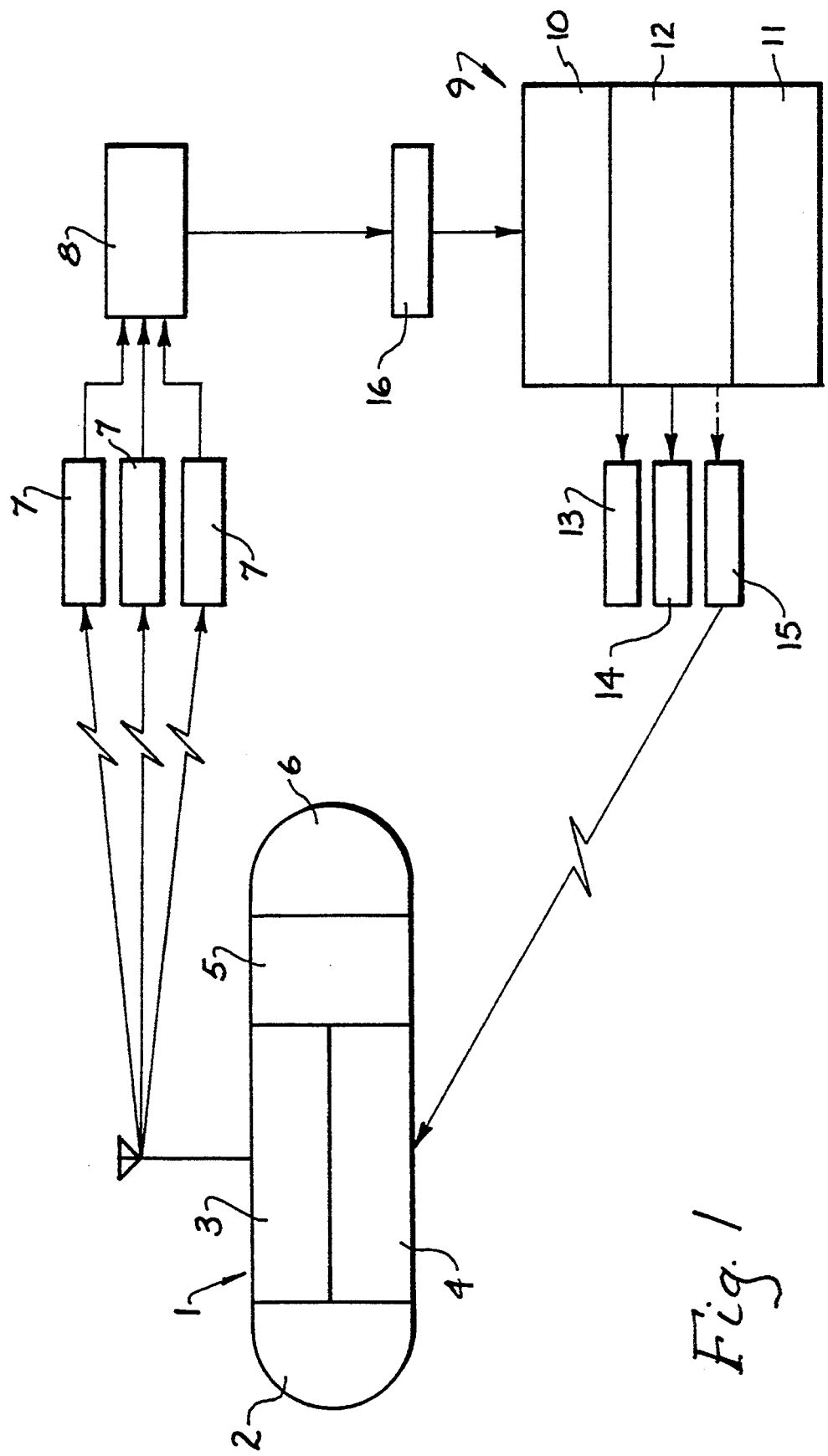
FIG. 1 is a schematic illustration of a typical system of the invention.
Figure 2:
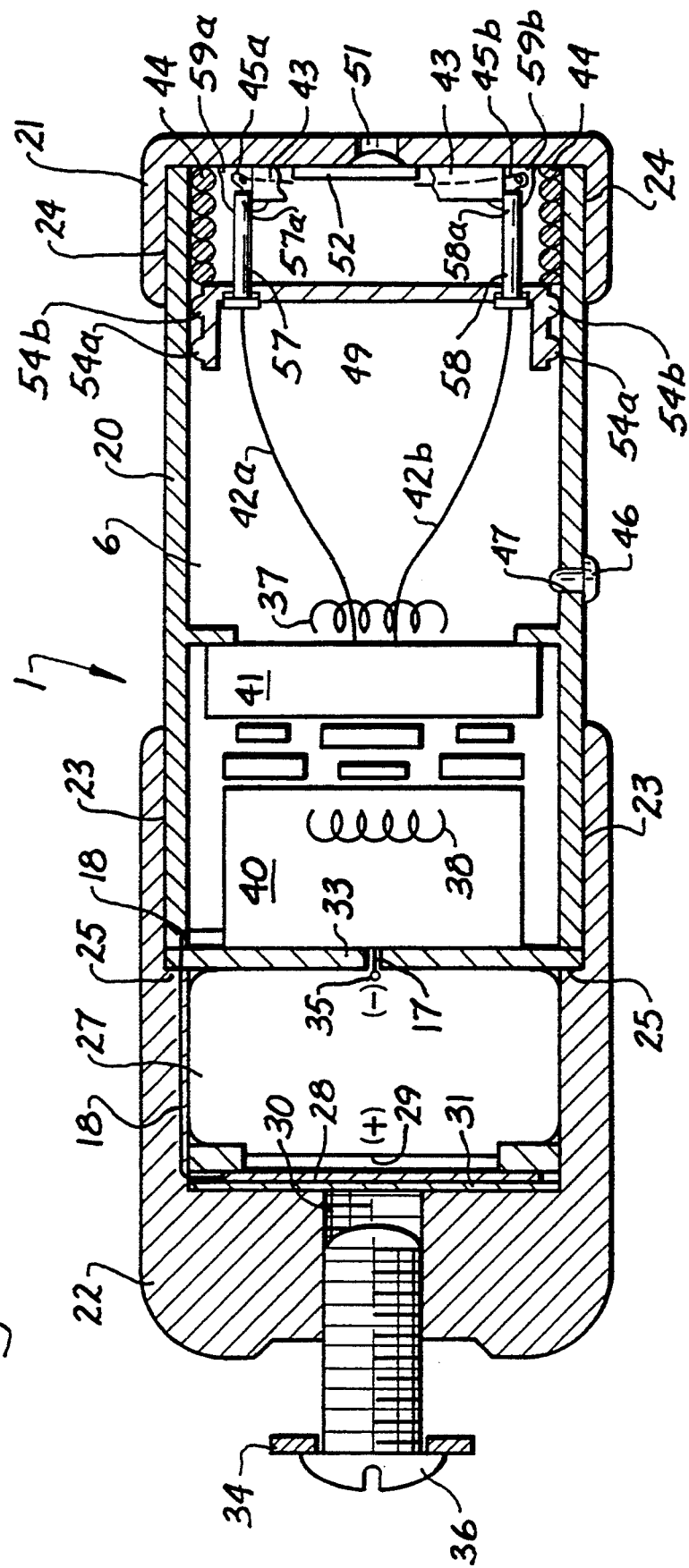
FIG. 2 is a sectional view of a typical capsule of the invention prior to enabling the power source.

FIG. 1 comprises a schematic illustration of the main components of the telemetry capsule system of the invention and the manner in which they are interrelated in general operation.

Therein, capsule 1, typically comprises an electric power source 2, radio signal transmitter 3, remote controlled actuator 4, sampling assembly 5 and sample storage compartment 6, which are interrelated to provide the two functions of transmittal of tracking data and fluid sample gathering.

In functioning to provide tracking data, transmitter 3, emits a radio signal(s) from the capsule that pass through the animal's body tissue, and are collected by antennae 7, located exterior to the body, which in turn feed collected signals to an appropriate receiver 8 which is remote from the capsule. Signals emitted from transmitter 3 are generally constant and generally need not vary in frequency, intensity or the like to provide adequate tracking data. Typically, multiple antennae are utilized in the system of the invention for collection of signals from the capsule radio signal transmitting means 3 to obtain precise positioning of the capsule in the alimentary canal through geometric triangulation in combination with an expert system based software. The antennae 7 can be located in non-mobile instrumentation to which the patient is confined, but, generally the multiple antennae are arranged about the body in a vest or belt type unit that allows the patient to move about in a wide range of daily activity.

Remote receiver 8, preferably miniaturized, is generally hard wired to the multiple antennae and receives the multiple signals collected thereby. The receiver may in turn be hard wired to one or more central processing units and non-volatile memory, or, may be in air wave radio communication through a transmitter with a further receiver, which in turn may be hard wired to a one or more central processing units.

Generally, the receiver or receiver/transmitter is mounted together with the antennae on the body and is hard wired to one or more central processing units. The central processing units are generally separate units to which the receiver is tethered, but may also be mounted on the body. The signal received by the transmitter is typically amplified, differentiated or otherwise distinguished and/or converted to digital data which can be used in the central processing unit for determining location of the capsule emitting the signals. This data, in turn, is typically internally stored within non-volatile memory for later review and analysis.

In a further embodiment of the invention, which would allow the patient maximum freedom, a first receiver-transmitter is mounted together with the antennae on the body and is in air wave radio communication with a second receiver that is hard wired to one or more central processing units. The signal received by the receiver, which is hard wired to the central processing unit, is processed in a similar fashion as that described above and as follows.

Central data processing unit 9 generally constitutes a computer or the like, typically comprising data distribution means 10, data storage means 11 and comparator/computing means 12. Data from the remote receiver 8 is typically routed to micro-controller means 16 then to distribution means 10, wherein it is distributed to comparator/computing means 12 and/or storage means 11. Comparator/computing means 12, generally compares data received from the distribution means with previously stored data and analyzes, computes and/or confirms geometric location of the capsule within the alimentary canal. Monitor 13 and/or printer 14 are typically provided to allow visual confirmation, to the operator, of the status and location of the capsule. Micro controller means 16 provides means for digitizing data from the antennae receiver instrumentation.

Upon receipt of signals from the capsule indicating alignment of the capsule at a specified site in the alimentary canal, the sample gathering function of the capsule is typically undertaken. To initiate sample gathering, remote trigger 15 transmits an actuating signal to the actuator of the capsule, which receives the signal and actuates the sampling assembly causing the fluids in the alimentary canal to be drawn into the capsule.

FIGS. 2–6 comprise sectional views of a typical capsule of the invention as it would appear before enabling of the power source through the completion of sampling. Therein, capsule 1, comprises generally cylindrical central shell 20, which generally contains the electronics and sampling assembly, sampling end cap 21 and power source end cap 22 assembled to form a non-digestible outer capsule shell. Sampling end cap 21 comprises filling opening 51 and filling flap assembly 52. Typically the end caps are sealed at 23 and 24, around central shell 20, using a non toxic glue or adhesive to prevent leakage of digestive tract fluids into the capsule and/or leakage of samples of fluids out of the capsule.

Power source end cap 22, generally comprises a battery, power source activating means and power transmission means for operating the electronics of the capsule.

In FIGS. 2–5, power source end cap 22 is shown as generally comprising a battery 27, having positive terminal 29 and negative terminal 35, deflectable positive bus disk 28, flexible disk seal 31, threaded screw hole 30, mating activating screw 36, sealing washer 34, transmission line 17, transmission line 18 and divider barrier 33. Shoulder 25 of end cap 22 is dimensioned to provide consistent placement of the power source end cap along the length of central shell 20. Transmission line 17 electrically connects negative battery terminal 35 to negative terminals (not shown) of the circuitry of transmitter 40 and activator 41. Transmission line 18 connects positive battery terminal 29, through bus disk 28, to positive terminals (not shown) of the circuitry of transmitter 40 and actuator 41.

Actuator 41 generally comprises activator receiver circuitry, generally illustrated as initiator coil 37, and activating circuitry which initiates the sampling process. Negative and positive terminals of the activator receiver are connected through transmission line 17 and 18 to the negative and positive battery terminals. Negative and/or positive terminals of the activating circuitry are connected through receiver enabled switching means (not shown) to the negative and/or positive battery terminal.

Figure 3:
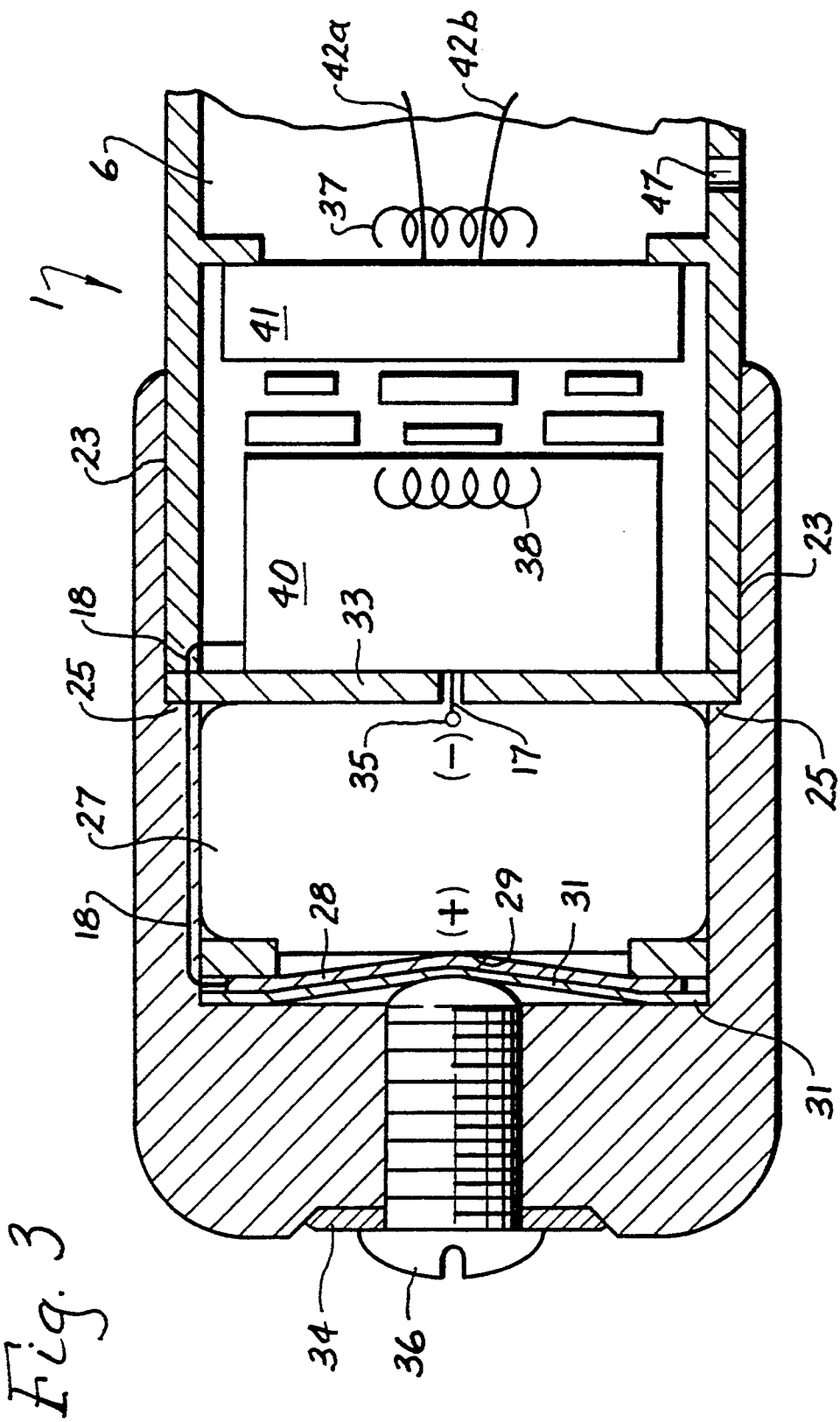
FIG. 3 is a sectional, fragmentary view of the enabled power source of the capsule of FIG. 2.

The capsule is activated for signal transmission and receipt prior to ingestion, and enabled, but not activated, for sampling as it progresses within the alimentary canal. FIG. 3 illustrates the enabling of the power source to electrically activate the capsule for signal transmission and receipt. Therein, activating screw 36 is adjusted inwardly to engage positive bus disk 28 and deflect same against positive terminal 29 of battery 27. Such adjustment completes the circuitry of transmitter 40 thus initiating radio signal transmission from the capsule. Such adjustment also completes the circuitry of the activator receiving portion, e.g. initiator coil 37 of activator 41 of the capsule, thus enabling the initiator coil to receive a signal transmitted to the capsule from a remote source. Flexible seal 31 and sealing washer 34 are arranged to resist seepage and/or flow of fluids from the alimentary canal through screw hole 30 to the battery. Interior divider 33 maintains battery 27 in position and generally insulates the battery from contact with the electronic components of the capsule.

In the process of the invention, activating screw 36 is adjusted to complete the above circuits just prior to ingestion of the capsule, and activation of the circuit completes electric so that the transmitter begins transmitting a suitable radio signal for collection by the antennae and the receiver is in an active mode awaiting an appropriate signal to enable activation of actuator 41.

Transmitter 40 operates independently of actuator 41 and is designed to emit a detectable radio signal, from transmission coil 38, upon completion of the circuit through activating screw 36. The radio signal may be constant or can be intermittent, but should be of sufficient intensity to be detectable in its passage through the animal body tissue to antennae located outside the body, by a receiver. Generally, a non-modulated signal, outside the broadcast range, is preferred. Typically there is no provision for switching off transmitter 40 and it remains in a transmitting mode throughout passage of the capsule through the alimentary tract.

Actuator 41 comprises a radio signal receiving means and activating circuitry. The activator receiving means is generally a single function receiver that completes a circuit to an "on" position, which enables activating means upon receipt of a defined activating transmission signal. The initiator coil generally is characterized by having a detectable resonate frequency and in a preferred embodiment of the invention, once the circuit is completed it stays in the "on" position through the remainder of the capsule's passage through the alimentary canal. The defined activating signal is generally transmitted by remote trigger 15.

Generally, the activating transmission signal is narrowly defined to prevent inadvertent activation by stray background radio signals. Upon receipt of an appropriate signal from remote trigger 15 of the system, actuator 41 generally directs power from the battery through power transmission lines 42a, 42b to filaments 45a and 45b. The use of the battery power by the actuator generally results in rapid dissipation of the energy available from the power source and typically transmission of detectable radio signals from the capsule will decrease in intensity and may cease to be detectable. This decrease or cessation of detectable radio signal is typically seen as confirmation that the sampling procedure has begun.

Figure 4:
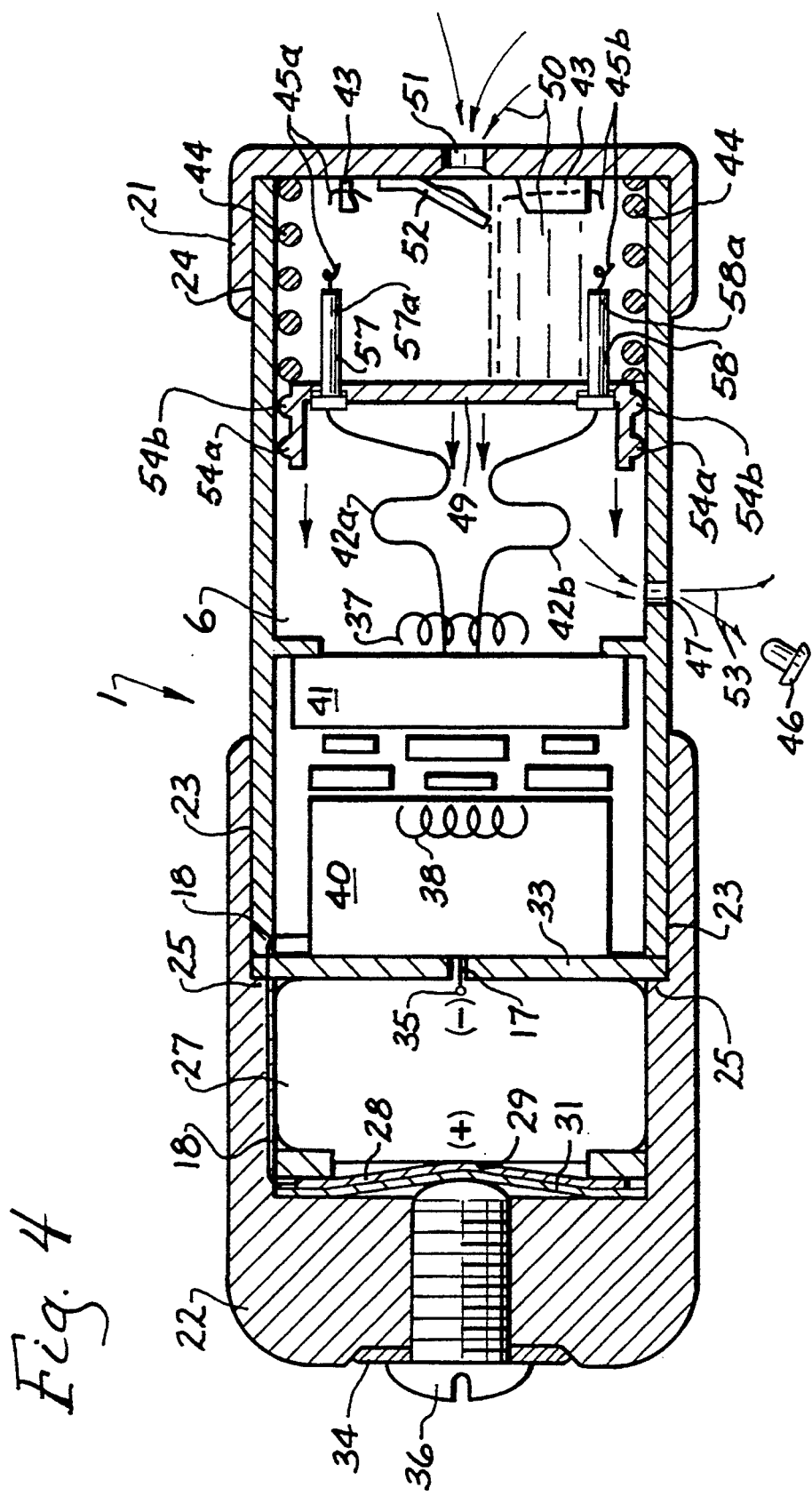
FIG. 4 is a sectional, partial fragmentary view of a capsule of FIG. 2, wherein sampling has been initiated.
Figure 5:
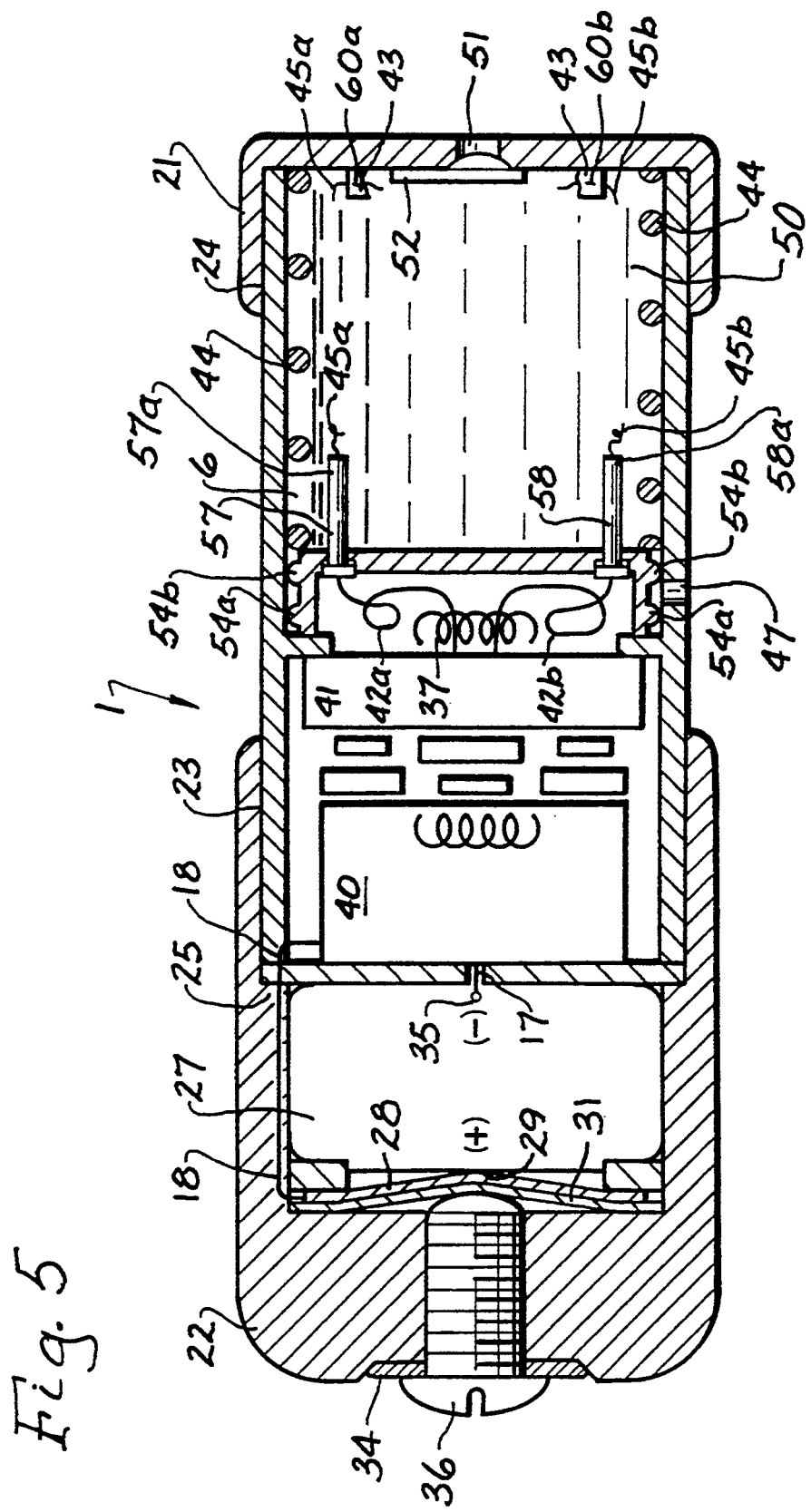
FIG. 5 is a sectional, partial fragmentary view of the capsule of FIG. 2 at the completion of sampling.
Figure 6:
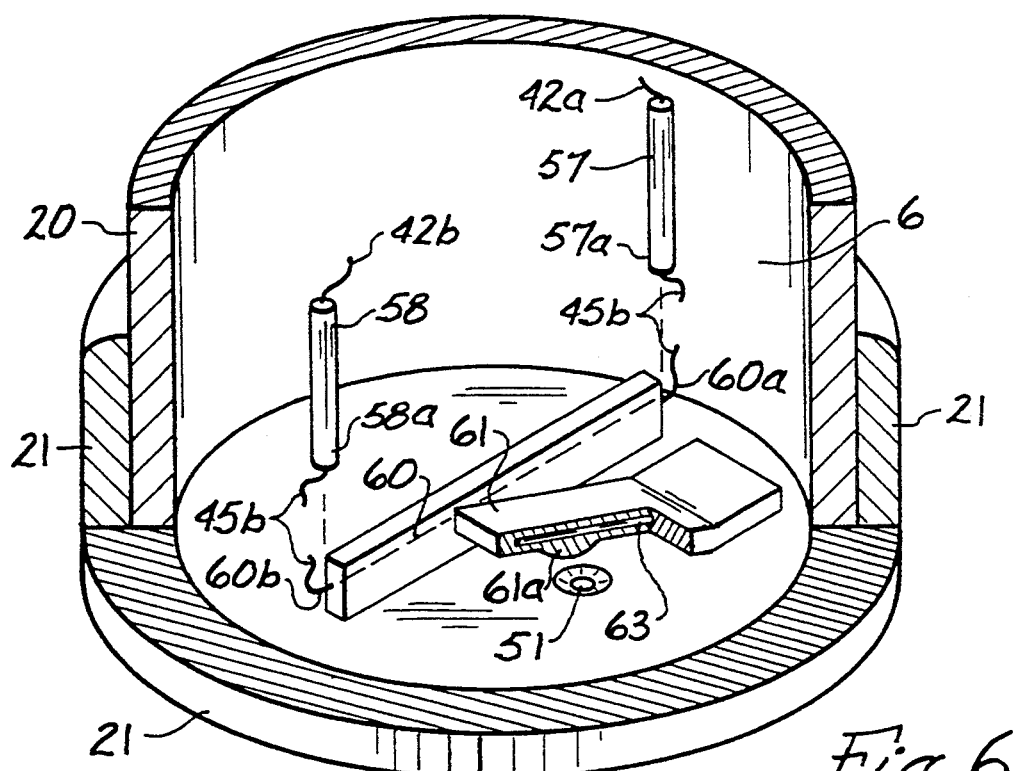
FIG. 6 is a sectional, partially exploded view of the sampling end cap portion of the capsule of FIG. 2.

FIGS. 4–6 illustrate the operation of the sampling assembly of the capsule. The sampling assembly generally comprises power transmission lines 42a and 42b, spring 44, blow out plug 46, air expulsion opening 47, piston 49, sampling filling opening 51 and sampling sealing flap assembly 52. Piston 49 comprises spaced sealing projections 54a and 54b, transmission wire guides 57 and 58, filaments 45a and 45b, and an electric current conductor arranged between the filaments generally referred to as glue bar 43.

In the non-activated stage, ends 57a and 58a of wire guides 57 and 58 are glued to end cap 21 by spots 59a and 59b of thermal sensitive adhesive or the like. In the embodiment shown, glue bar 43 constitutes the electric current conductor arranged between filaments 45a and 45b, comprising a conductor connecting the filaments and having ends configured to provide structural gluing surfaces for enhancing the adhesion of ends 57a and 58a to the end cap. Glue bar 43 may be comprised of conductive material or comprise a conductive element or the like which connects with filaments 45a and 45b, in activating circuitry among power transmission lines 42a and 42b. The filaments are imbedded in thermal glue spots 59a and 59b in an arrangement such that upon imposing a current therethrough they heat the glue spots sufficiently to cause release of ends 57a and 58a of wire guides 57 and 58 from cap 21.

In the process of the invention, upon actuation, actuator 41 completes the activating circuit from the power source through transmission lines 42a and 42b, filaments 45a and 45b and the conductor of glue bar 43. The filaments heat up, weaken the thermal sensitive adhesive of the glue spots such that the force of expanding coil spring 44 will cause ends 57a and 58a of transmission wire guides 57 and 58 to release from end cap 21.

Piston 49 is mounted in sampling compartment 6 in a initial forward position, arranged so that it will forcibly move from the forward position to a rearward position upon release of coil spring 44. The piston comprises spaced sealing projections 54a and 54b which sufficiently resist a flow of fluid around the piston such that upon rearward movement of the piston a partial vacuum is promoted in the forward portion of the sampling compartment and air in the rearward portion of the sampling compartment is compressed.

In operation of the sampling apparatus, the heating of the thermal sensitive glue spots by imbedded filaments 45a and 45b, weakens the adhesion of ends 57a and 58a of wire guides 57 and 58 with end cap 21 such that loaded coil spring 44 uncoils, pushes against piston 49 and moves the piston from its initial forward position in sampling compartment 6 to a rearward position. The rearward movement of piston 49 compresses the air in the rearward portion of compartment 6 and the resulting pressure causes the expulsion of blow out plug 46 from air relief opening 47 of the capsule and expulsion of air therefrom. Coincidentally, the retraction of piston 49 creates a partial vacuum in the forward portion of sampling compartment 6 which causes a sealing flap of assembly 52 to open inwardly and fluids 50 to be drawn into the front portion of the sample compartment through opening 51.

In FIG. 4, the remote trigger has signaled the actuator which closes a circuit from the power source and imposes a current through transmission lines 42a and 42b causing heat to be generated along filaments 45a and 45b which heats thermal glue spots 59a and 59b, weakening the adhesion of ends 57a and 58a to cap 21, and allowing the force of loaded spring 44 to push piston 49 rearward, coincidentally breaking filaments 45a and 45b. The rearward movement of piston 49 creates a partial vacuum in the front portion of the sample compartment and causing the flap of sealing flap assembly 52 to uncover sampling opening 51, allowing entry of fluid 50 from the alimentary canal, while compressed air in the rearward portion of the capsule causes blow out plug 46 to blow out of air relief opening 47 and the air 53 to escape from the capsule.

In FIG. 5, piston 49 has been forced to its rearmost position by uncoiling spring 44. In such position, spaced sealing projections 54a and 54b flank air relief opening 47 and restrain the air from further escape from the capsule. The pressure within the front portion of sampling compartment 6 equalizes with the pressure in the alimentary tract and the flap of sealing flap assembly 52 closes to seal sampling opening 51 and trap the fluid sample within the capsule.

Breaking of filaments 45a and 45b creates a detectable change in the resonate frequency of the activator circuit which can be monitored as a detectable indicator signal of sampling initiation.

FIG. 6 illustrates the relative positioning of the sealing flap assembly, filling opening, wire guides, filaments and glue bar with end cap 21. Therein glue bar 43 is shown as comprising a conductive wire 60 which connects at ends 60a and 60b to filaments 45a and 45b respectively. The other end of filaments 45a and 45b connect to power transmission lines 42a and 42b respectively which emerge from ends 57a and 58a of wire guides 57 and 58. Sealing flap assembly comprises flap 61, glue block 62 and spring assist 63. Flap 61 is formed from an elastomeric compound or the like. Spring assist 63 is a longitudinally extending spring element which engages glue block 62 and assists in maintaining flap 61 against filling opening 51. In a preferred embodiment flap 61 comprises a projection 61a thereon which seats in filling opening 51.

Figure 7:
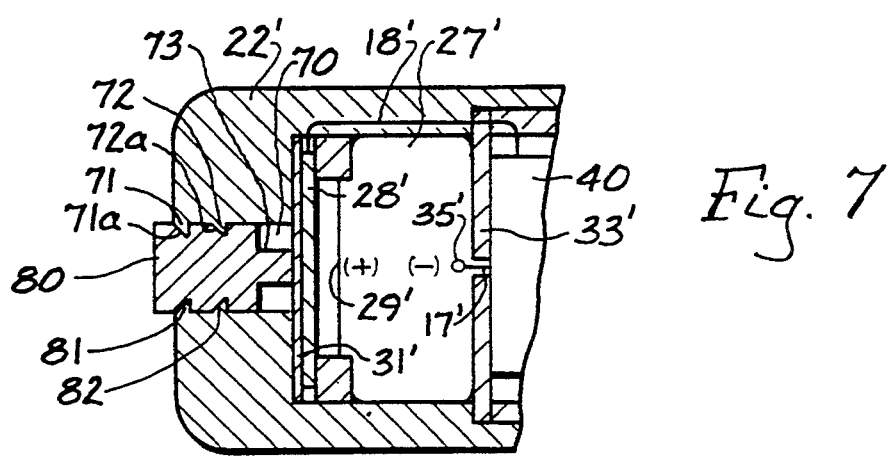
FIG. 7 is a partial sectional view of an alternate embodiment of a power source end cap arrangement of the capsule of FIG. 2 before electrical activation.
Figure 8:
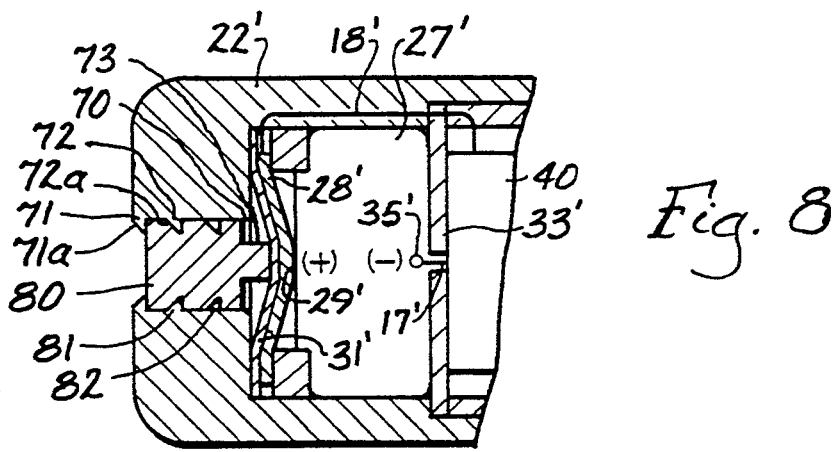
FIG. 8 is a partial sectional view of the alternate embodiment of a power source end cap of the capsule of FIG. 7 upon electrical activation.

FIGS. 7 and 8 illustrate another embodiment of the power source activating means. End cap 22' is shown as generally comprising battery 27', having positive terminal 29' and negative terminal 35', deflectable positive bus disk 28', flexible disk seal 31', hole 70, activating member 80, divider barrier 33' and transmission lines 17' and 18'. End cap 22' is formed from polymeric material and hole 70 comprises spaced projections 71 and 72, which are beveled at 71a and 72a to enhance deflection and enable forced insertion of activating member 80 in hole 70. Activating member 80 is an elongated member comprising major and minor cylindrical diameters. The minor diameter 73 is sized to engage flexible disk seal 31' for deflecting positive bus disk 28' against terminal 29' of battery 27'. Major diameter 74 comprises circumferential slots 81 and 82, which are in spaced mating alignment with projections 71 and 72 of hole 70, and sized to mate with projections 71 and 72 upon forced insertion of member 80 in activating means hole 70. Thus, in a first non-activated forcibly inserted position as shown in FIG. 7, the minor diameter of activating member 80 does not deflect bus disk 28', but when further inserted as shown FIG. 8, bus disk 28' is deflected against positive terminal 29'.

Figure 11:
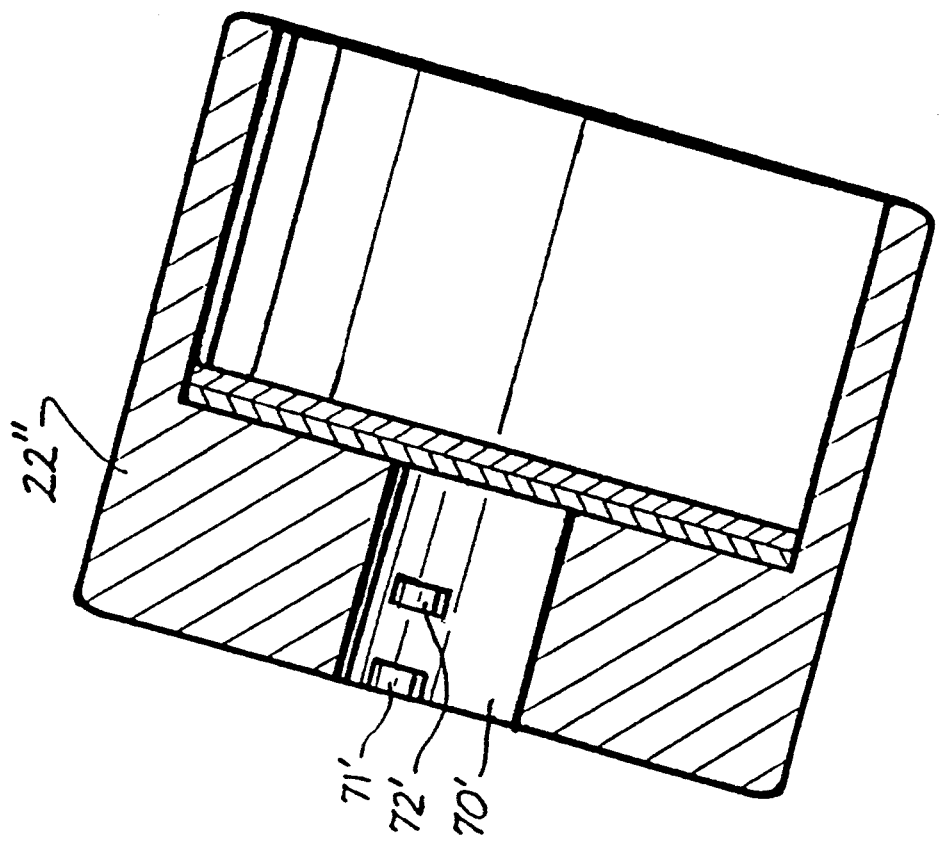
FIG. 11 is a sectional view of a power supply end cap for use with the activating member of FIG. 10.
Figure 10:
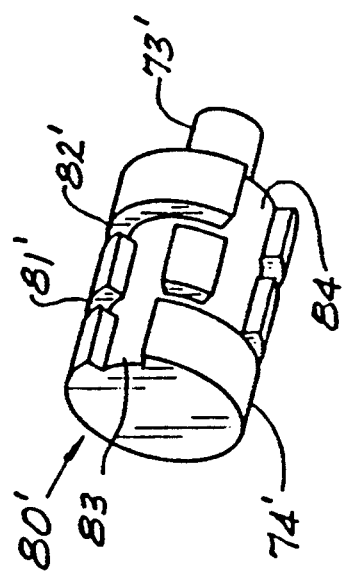
FIG. 10 is a perspective view of an alternate embodiment of an activating member of the invention.

FIGS. 10 and 11 illustrate a further embodiment of the power source activating means. In FIG. 10, activating member 80' is an elongated member comprising minor and major cylindrical diameters 73' and 74' respectively. The minor diameter 73' is sized for engagement with the flexible disk seal and activating the power source by deflecting the positive bus disk against the positive terminal of the battery. The major diameter 74' comprises circumferential slots 81' and 82', which are spaced for mating alignment with projections 71' and 72' of hole 70' of end cap 22" of FIG. 11. Longitudinal slots 83 and 84 of activating member 80' are arranged for insertion of member 80' into hole 70' by being sized to mate with projections 71' and 72' and enabling stepped insertion of member 80 to a none activated partially inserted position to an activated fully inserted position in hole 70'. Thus, in a first non-activated position member 80' is inserted such that circumferential slots 81' and 82' align with projections 71' and 72' respectively and in an activated position member 80' is rotated and further inserted in end cap 22" such that slot 81' aligns with projection 72'.

Figure 9:
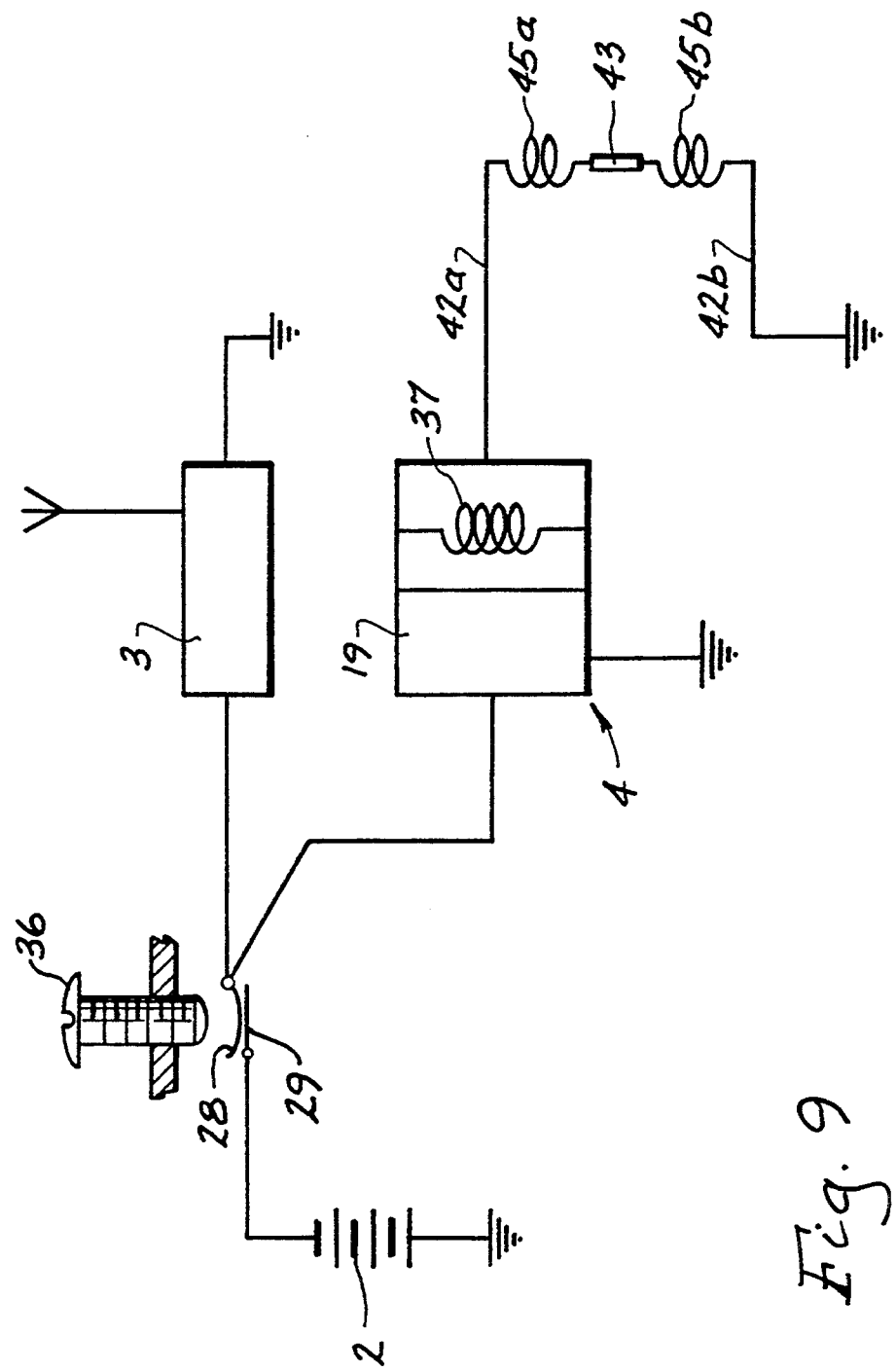
FIG. 9 is a schematic illustration of the sampling activating system of the capsule.

FIG. 9, comprises a block diagram illustrating typical circuitry of a capsule of the invention. Therein, is illustrated that upon engaging of bus disk 28 against positive terminal 29 through adjustment of activating screw 36, the circuitry of radio signal transmitting means 3 is completed and the transmitting means is powered, by electric power source 2, to begin emitting radio signals and continue same, until the power from the power source is dissipated. At the same time the circuit of receiver 19 of remote controlled actuator 4 is enabled but not powered, such that upon receiving a proper signal from a remote trigger, receiver 19 actuates initiator coil 37 of actuator 4 and causes current to flow through transmission line 42a, filament 45a, glue bar 43, filament 45b and transmission line 42b to ground, causing the filaments to heat up, the glue spots to fail, the piston to be released for movement by the spring. It should be noted that preferably, deactivation of the transmitter circuit does not occur upon actuation of initiator coil 37.

A wide variety of electric power sources can be used in the capsule of the instant invention. Generally, such means can comprise a storage battery or can also comprise an electric generating device that is activated during use of the capsule. Typically, modern mercury, silver oxide, NiCad and lithium batteries are suitable in size and energy storage for use in the capsule of the present invention.

Similarly, mechanical power generators might be used in the capsule of the invention, such as tensioned spring electric generating devices and the like. Such devices must be subminiature in size and the number of moving parts required reduces the probability of their widespread use. Radioisotope power sources have been suggested as electric power supply means for subminiature utilities, however such means are not yet commercially available for use.

In another embodiment of the instant invention, a chemical and/or biological fuel cell comprises the power source, such as yeast metabolites reacting with an electrode material.

Generally the capsule can be formed from any suitable material that will resist degradation while passing through the alimentary canal. Generally, a polycarbonate material is preferred for the outer shell. Various liquid, solid, slurry or gaseous samples may be taken with the capsule and process of the invention. Generally the capsule and process operate more effectively taking liquid, liquid slurry or gaseous samples.

Radio signal transmitting and receiving means suitable for use in the capsule of the invention are well known in the art. Sub-miniature radio transmitters as described by A. M. Connell in GUT, 1960, 1, pp 266 and H. G. Noller, in Medical Electronics, 1960, pp 342 appear suitable for the capsule of the invention.

The remote receiver and antennae are generally seen as comprising a receiver subsystem for the purposes of the invention. Typically, such receiver subsystem used in the process of the invention comprises multiple dipole antennae, the outputs of which are time multiplexed to a computer tuned superheterodyne receiver and quadrature detector.

In the general operation of a typical receiver subsystem of the invention, the output from multiple dipole antennae, typically about eight, are matched in impedance by processing through a common impedance matching network. The matched output of the antennae are then time multiplexed, by means of data input control from the computer and the multiplexed signal is channeled to a radio frequency (RF) amplifier of the receiver for amplification. The amplified signal is then channeled to the computer tuned superheterodyne receiver where it is typically filtered to remove spurious signals and then implied to an RF input of a mixer to convert it to an intermediate frequency signal for convenient processing. The intermediate frequency signal is directed to a quadrature detector that confirms received signal validity, with valid signals being then digitized by the receiver for transmittal to the computer. The intermediate frequency output of the mixer is also amplified, and applied by the receiver to an absolute value circuit to quantify signal strength as a DC voltage signal representing relative received signal strength from each antenna and is transmitted to the computer.

Receivers which can detect the presence of a valid input frequency, measure the relative strength of the signal, amplify, detect and digitize the signal are commonly available and typically used as communications receivers.

The computer subsystem generally comprises a commonly available instrument micro-controller and a typical central processing unit which includes a distribution means, comparator/computer, data storage means, monitor, printer and appropriate software.

In the general operation of the process, the digitized valid signals confirm continuing identification of the capsule and the DC voltage signal from each antenna is digitized by the micro-controller to provide capsule location input to the central processing unit. Thus as a sampling capsule moves through the alimentary canal the variations in quantified DC voltage signal, derived from each antenna and digitized by the micro-controller, are compared by the software of the central processing unit to the digitized historic DC voltage signal data obtained from the previous passage of a non-sampling capsule. In addition to the direct comparison of digitized non-sampling historic DC voltage signal data, comparison may be made with other factors such as length of time in the canal, active antennae group, historic progress rate through the canal, rate and/or time models, normalized or model voltage signal data and the like. Typically, the software scans and computes variations from the non-sampling historic signal data, together with variations from one or more other factors, in pre-programmed weighted relation to establish a calculated probability of geometric location of the sampling capsule. Typically the calculated probability is continually monitored by the central processing unit and upon variation beyond pre-programmed limits will scan and recalculate discarding and/or incorporating other factors as may be pre-programmed into the software.

Such recalculating, discarding and/or incorporating of other factors is generally referred to as the expert system of the software for purposes of this application. Typically, the software is pre-programmed to signal the operator or otherwise initiate sampling when the calculated geometric location conforms to the pre-programmed desired location within pre-defined limits of probability. The exceeding of such pre-defined limits of probability, even in view of scanning and recalculation, is also typically signaled to the operator to indicate failure of accurate location.

The components of the remote trigger and the release verification system remote from the capsule are generally considered the sampling initiator and verification subsystem for purposes of the invention. Typically such subsystem comprises an initiator coil, initiator pulse amplifier, transmit/receive (TR) switch and a sampling verification grid dip module in the RF receiver.

In typical operation of the process of the invention, the computer signals when initiation of sampling is appropriate. The initiator pulse amplifier acts to shape and amplify a pulse from the initiation signal and sends it to the initiator coil, which acts as a transmitting antenna to transmit the amplified pulse to the actuator of the capsule. The TR switch is typically located before the multiplexer of the multiple dipole antennae and disconnects the multiple antennae from the multiplexer while the pulse amplifier is in operation to prevent damage to the low level circuitry of the RF receiver, particularly the grid dip module, from the high powered pulse.

After the amplified pulse has been transmitted the TR switch reconnects the antennae to the multiplexer and the grid dip module senses the resonate frequency of the activator circuit of the capsule.

Typically, the operation of the initiator pulse amplifier and TR switch are inter-controlled by the central processing unit. The data corresponding to the changes or failure to change frequency is transmitted by the receiver to the CPU and the software can be preprogrammed to re-initiate the sequence, indicate sampling success or failure, as may be desired.

While various particular embodiments of the invention have been shown and described, it will, of course be understood that various modifications can be made without departure from the principles of the invention.

We claim:

1. An ingestible capsule for removal of a fluid sample from the alimentary canal of an animal comprising, an electric power source; a radio signal transmitting means in enabling circuitry with said power source, said transmitting means being suitable for transmitting a radio signal the location from which the transmission emanates being trackable through animal tissue; a fluid sample storage compartment; means for obtaining a fluid sample from said alimentary canal; all encased in an essentially non-digestible outer shell that is configured to pass through said alimentary canal.

2. The capsule of claim 1 wherein said means for obtaining said fluid sample is actuatable remote from said capsule.

3. The capsule of claim 1 wherein said electric power source comprises a battery.

4. The capsule of claim 1 wherein said transmitting means emits a radio signal, detectable exterior of said outer shell of said capsule when enabled by said power source.

5. The capsule of claim 2 wherein said means for obtaining said fluid sample is actuatable by radio signal transmitted from a site exterior of the body of said animal.

6. The capsule of claim 1 wherein said enabling circuitry comprises switching means.

7. The capsule of claim 1 comprising a passageway for the flow of fluid from the exterior of said capsule to the interior of said capsule.

8. The capsule of claim 7 comprising means arranged to resist the flow of fluid through said passageway.

9. The capsule of claim 8 wherein said means arranged to resist the flow of fluid comprises a one way flap means.

10. The capsule of claim 7 wherein said passageway comprises a closable opening through said outer shell to a storage compartment within said capsule, said closable opening comprising a spring assisted one way valve means.

11. The capsule of claim 1 wherein said means for obtaining a fluid sample comprises activating means arranged to initiate sampling activity of a sampling means.

12. The capsule of claim 11 wherein said activating means comprises means for receiving a radio signal transmitted from a site exterior of the body of said animal.

13. The capsule of claim 11 wherein said activating means comprises an initiator coil that is characterized by a detectable resonate frequency when activated.

14. The capsule of claim 12 comprising means for enabling the flow of electricity from said power source to said sampling means in response to receiving said radio signal from a site exterior said body.

15. The capsule of claim 14 wherein said sampling means comprises a filament, which is arranged to heat a thermal sensitive adhesive when the flow of electricity from said power source is enabled.

16. The capsule of claim 15 wherein said thermal sensitive adhesive is comprised in an arrangement which restrains a spring, and heating of said adhesive by said filament releases said restraint.

17. The capsule of claim 16 wherein said sampling means comprises a piston which is arranged in said sample storage compartment, release of said spring urges said piston from a first position in said compartment to a second position, and the movement of said piston creates a partial vacuum in a portion of said storage compartment which influences the flow of a fluid from said alimentary canal through a passageway in said capsule to said portion of said storage compartment.

18. The capsule of claim 17 wherein said filament breaks through movement of said piston and the flow of electricity therethrough is disconnected.

19. The capsule of claim 18 wherein breaking said filament changes the resonate frequency of said initiator coil.

20. The capsule of claim 1 wherein said sampling means comprises a movable piston adapted to influence the flow of a fluid from the alimentary canal into said capsule, through movement of said piston from a first position to a second position.

21. The capsule of claim 20 wherein said movement of said piston creates a pressure in a portion of said capsule.

22. The capsule of claim 21 comprising means for relieving said pressure in said portion of said capsule.

23. The capsule of claim 22 wherein said means for relieving said pressure comprises a pressure induced opening to the exterior of said capsule through which air can flow, and movement of the piston to a said second position restrains said flow of air through said opening.

24. The capsule of claim 23 wherein said piston comprises means for restraining the flow of fluid through said opening.

25. The capsule of claim 20 wherein said piston is arranged in said sample storage compartment and movement of said piston from said first position to a second position influences the flow of a fluid from the alimentary canal into said storage compartment.

26. The capsule of claim 25 wherein said movement of said piston creates a partial vacuum in a portion of said storage compartment which influences the flow of a fluid from said alimentary canal through a passageway from the exterior of said capsule into said portion of said storage compartment.

27. The capsule of claim 1 wherein said outer shell comprises a polycarbonate.

28. An ingestible capsule for removal of a fluid sample from the alimentary canal of an animal comprising, a non-digestible outer shell; an electric power source; a radio signal transmitting means; and a fluid sample storage compartment comprising a piston means arranged for withdrawing a fluid sample from said alimentary canal in response to a signal from a signal means remote from the body of said animal.

29. An ingestible capsule for sampling a fluid from the alimentary canal of an animal comprising, a non-digestible outer shell; an electric power source; a first radio signal transmitting means; a fluid sample storage compartment; means for receiving a second radio signal; and, a fluid sampling means responsive to the receipt of said second radio signal.

30. The capsule of claim 29 wherein said fluid sampling means withdraws fluid from said alimentary canal through differential pressure means.

31. The capsule of claim 29 comprising a fluid sample taken from said alimentary canal.

32. A process for the gathering of a fluid sample from a selected site in the alimentary canal of an animal comprising, providing an ingestible capsule containing a signal transmitting means and a remote actuatable fluid sampling means; ingesting said capsule into the alimentary canal; transmitting a signal, trackable through animal tissue, from said transmitting means contained in said capsule, said signal being suitable for determining location of said capsule; receiving said transmitted signal exterior of the body of said animal; comparing said signal to a pre-established model; transmitting an actuating signal to said remote actuatable fluid sampling means contained in said capsule; and gathering a fluid sample in said capsule in response to said actuating signal.

33. The process of claim 32 wherein said signal is a radio signal.

34. The process of claim 33 wherein said radio signal, transmitted from said transmitting means in said capsule, is converted to an intermediate frequency signal.

35. The process of claim 34 wherein an intermediate frequency signal is quantified as a DC voltage signal.

36. The process of claim 35 wherein a quantified DC voltage signal is digitized to provide input to a computer.

37. The process of claim 32 wherein a radio signal is transmitted from said transmitting means in said capsule and is received at multiple receiving antennae arranged about the exterior of the body of said animal.

38. The process of claim 37 wherein the output of said multiple receiving antennae is directed to time multiplexing means and said output is converted to time multiplexed output.

39. The process of claim 38 wherein a time multiplexed output of the multiple receiving antennae is converted to an intermediate frequency signal, quantified as a DC voltage signal and digitized to provide input to a computer.

40. The process of claim 32 where digitized information from said transmitted signal is compared to digitized information from said pre-established model in a computer.

41. The process of claim 32 wherein said pre-established model comprises historic data obtained from the previous passage of a radio signal transmitting capsule through said alimentary canal.

42. The process of claim 32 wherein said pre-established model comprises digitized information having parameters comprising one of a rate of progress of said capsule through said canal, length of time of said capsule in said canal or normalized model.

43. The process of claim 32 wherein sampling of said fluid initiates a sampling indicator signal, by sampling indicator means comprised in said capsule, which is detectable exterior of the body of said animal.

44. The process of claim 32 wherein said transmitted signal is received exterior of the animal body, digitized and provided to a computer.

45. The process of claim 44 wherein said pre-established model comprises digitized historic data obtained from the previous passage of a capsule through said alimentary canal.

46. The process of claim 44 wherein said pre-established model comprises one of a rate of progress of said capsule through said canal, length of time of said capsule in said canal or normalized model.

47. The process of claim 44 wherein said computer is programmed to scan and compute variations from pre-programmed factors.

48. The process of claim 44 wherein transmission of said activating signal is operator controlled.

49. The process of claim 44 wherein said computer is programmed to initiate an actuating signal to the fluid sampling means of the capsule.

50. The process of claim 49 wherein sampling of said fluid initiates a sampling indicator signal, by sampling indicator means comprised in said capsule, which is detectable exterior of the body of said animal.

51. The process of claim 50 wherein said computer is programmed to re-initiate an activating signal when a sampling indicator signal is not received from said capsule after an actuating signal has been initiated by said computer.

52. The process of claim 32 comprising two or more capsules in the alimentary canal transmitting differential signals.

53. The process of claim 32 wherein a first ingestible capsule, containing a signal transmitting means, is ingested into said alimentary canal; a signal transmitted from said first capsule is received exterior of said body and digitized in a computer; and digitized data from said signal transmitted from said first capsule comprises said pre-established model.

54. A process for the collection of data for the sampling of a fluid at a selected site in the alimentary canal of an animal comprising, providing an ingestible capsule containing a radio signal transmitting means suitable for determining location of said capsule; ingesting said capsule into the alimentary canal; transmitting a radio signal from said transmitting means; receiving said transmitted signal exterior of the body of said animal at multiple receiving antennae arranged about said canal; digitizing said signal received by said multiple receiving antennae; storing said digitized signal in computer recoverable, time sequence memory.

55. The process of claim 54 wherein said stored digitized signal is compared to digitized data derived from transmitted signals from the passage of another capsule through said alimentary canal.

* * * * *

(12) EX PARTE REEXAMINATION CERTIFICATE (5435th)
United States Patent
D'Andrea et al.

(10) Number: US 5,395,366 C1
(45) Certificate Issued: Jul. 4, 2006

(54) SAMPLING CAPSULE AND PROCESS

(75) Inventors: David T. D'Andrea, Amherst, NY (US); Jerome J. Schentag, Eggertsville, NY (US)

(73) Assignee: Gastrotarget Corp., Tonawanda, NY (US)

Reexamination Request:
No. 90/006,783, Sep. 25, 2003

Reexamination Certificate for:
Patent No.: 5,395,366
Issued: Mar. 7, 1995
Appl. No.: 08/179,502
Filed: Jan. 10, 1994

Related U.S. Application Data

(63) Continuation-in-part of application No. 07/707,842, filed on May 30, 1991, now Pat. No. 5,279,607.

(51) Int. Cl.
*A61K 9/22* (2006.01)

(52) U.S. Cl. .................. 604/890.1; 604/114; 604/891.1; 604/93.01

(58) Field of Classification Search .................. None
See application file for complete search history.

(56) References Cited

U.S. PATENT DOCUMENTS

| | | | | |
|---|---|---|---|---|
| 3,118,439 A | * | 1/1964 | Perrenoud | 600/582 |
| 3,315,660 A | * | 4/1967 | Abella | 600/582 |
| 3,485,235 A | * | 12/1969 | Felson | 600/582 |
| 4,239,040 A | * | 12/1980 | Hosoya et al. | 604/135 |
| 4,439,197 A | * | 3/1984 | Honda et al. | 604/891.1 |
| 4,481,952 A | * | 11/1984 | Pawelec | 600/582 |
| 4,507,115 A | * | 3/1985 | Kambara et al. | 604/135 |
| 5,167,626 A | * | 12/1992 | Casper et al. | 604/891.1 |
| 5,217,449 A | * | 6/1993 | Yuda et al. | 604/890.1 |
| 5,279,607 A | * | 1/1994 | Schentag et al. | 604/890.1 |
| 5,316,015 A | * | 5/1994 | Sinaiko | 600/582 |

FOREIGN PATENT DOCUMENTS

EP 0 460 327 A1 * 11/1991

* cited by examiner

*Primary Examiner*—Nicholas D. Lucchesi

(57) ABSTRACT

An ingestible capsule and process for sampling, particularly repeatable sampling, of fluids in the alimentary canal is disclosed wherein an essentially non-digestible capsule contains an electric energy emitting means, a radio signal transmitting means, a sampling storage means and a remote actuatable sampling means. The capsule signals a remote receiver as it progresses through the alimentary tract in a previously mapped route and upon reaching a specified site is remotely triggered to capture a fluid sample in the alimentary canal.

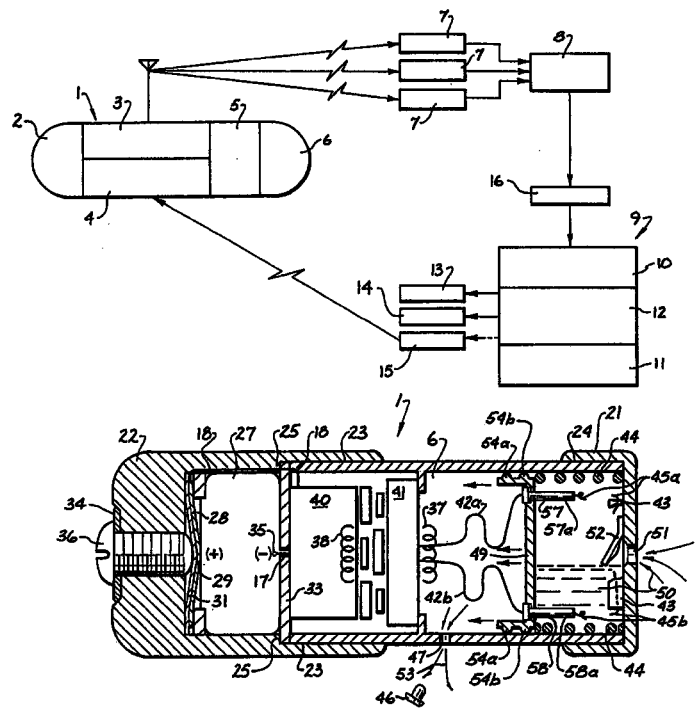

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY THE AMENDMENT ARE PRINTED HEREIN:

Column 11, lines 34–37:

After the amplified pulse has been transmitted, the TR switch reconnects the antennae to the multiplexer and the grid dip module senses the [resonate] *resonant* frequency of the activator circuit of the capsule.

AS A RESULT OF REEXAMINATION, IT HAS BEEN DETERMINED THAT:

Claims 7, 28, 43, 54 and 55 are cancelled.

Claims 1, 8–10, 13, 15, 19, 20, 23, 25, 29, 32, 35, 38, 39, 48 and 49 are determined to be patentable as amended.

Claims 2–6, 11, 12, 14, 16–18, 21, 22, 24, 26, 27, 30, 31, 33, 34, 36, 37, 40–42, 44–47 and 50–53, dependent on an amended claim, are determined to be patentable.

1. An ingestible capsule for removal of a fluid sample from the alimentary canal of an animal, comprising[.]*:*
   an electric power source;
   a radio signal transmitting means in enabling circuitry with said power source, said transmitting means being suitable for transmitting a radio signal, the location from which the transmission emanates being trackable through animal tissue;
   a fluid sample storage compartment;
   means for obtaining a fluid sample from said alimentary canal;
   [all] *a* fluid flow passageway communicating said storage compartment with the exterior of said capsule; *and*
   *a one-way valve arranged in said passageway;*
   *said capsule being* encased in an essentially non-digestible outer shell that is configured to pass through said alimentary canal.

8. The capsule of claim [7 comprising means arranged to resist] *1 wherein said valve is an impedance to* the flow of fluid through said passageway.

9. The capsule of claim [8] *1* wherein said [means arranged to resist the flow of fluid comprises] *valve is a* one-way flap [means] *valve*.

10. The capsule of claim 7 wherein said passageway comprises a closable opening through said outer shell to a storage compartment within said capsule, said closable opening comprising a spring-assisted one-way valve [means].

13. The capsule of claim 11 wherein said activating means comprises an initiator coil that is characterized by a detectable [resonate] *resonant* frequency when activated.

15. The capsule of claim 14 wherein said sampling means comprises a filament[,] which is arranged to heat a thermal sensitive adhesive when the flow of electricity from said power source is enabled.

19. The capsule of claim 18 wherein breaking said filament changes the [resonate] *resonant* frequency of said initiator coil.

20. The capsule of claim 1 wherein said sampling means comprises a movable piston adapted to influence the flow of a fluid from the alimentary canal into said capsule[,] through movement of said piston from a first position to a second position.

23. The capsule of claim 22 wherein said means for relieving said pressure comprises a pressure-induced opening to the exterior of said capsule through which air can flow, and *wherein* movement of the piston to a said second position restrains said flow of air through said opening.

25. The capsule of claim 20 wherein said piston is arranged in said sample storage compartment and movement of said piston from said first position to [a] *said* second position influences the flow of a fluid from the alimentary canal into said storage compartment.

29. An ingestible capsule for sampling a fluid from the alimentary canal of an animal, comprising[.]*:*
   a non-digestible outer shell;
   an electric power source;
   a first radio signal transmitting means;
   a fluid sample storage compartment;
   means for receiving a second radio signal; and[.]
   a fluid sampling means responsive to the receipt of said second radio signal.

32. A process for the gathering of a fluid sample from a selected site in the alimentary canal of animal comprising[,] *the steps of:*
   providing an ingestible capsule containing a signal transmitting means and a remote actuatable fluid sampling means;
   ingesting said capsule into the alimentary canal;
   transmitting a signal, trackable through animal tissue, from said transmitting means contained in said capsule, said signal being suitable for determining *the* location of said capsule;
   receiving said transmitted signal exterior of the body of said animal;
   comparing said signal to a pre-established model;
   transmitting an actuating signal to said remote actuatable fluid sampling means contained in said capsule; [and]
   gathering a fluid sample in said capsule in response to said actuating signal; *and indicating that fluid has been sampled, by means of a sampling indicator means contained in said capsule, which is detectable exterior of the body of said animal.*

35. The process of claim 34 wherein [an] *said* intermediate frequency signal is quantified as a DC voltage signal.

38. The process of claim 37 wherein [the] *said multiple receiving antennae have an output, and wherein said* output [of said multiple receiving antennae] is directed to time multiplexing means and said output is converted to time multiplexed output.

39. The process of claim 38 wherein [a] *said* time multiplexed output [of the multiple receiving antennae] is converted to an intermediate frequency signal, quantified as a DC voltage signal and digitized to provide input to a computer.

48. The process of claim 44 wherein transmission of said [activating] *actuating* signal is operator controlled.

49. The process of claim 44 wherein said computer is programmed to initiate [an] *said* actuating signal to the fluid sampling means of the capsule.

* * * * *